United States Patent

Cohnen et al.

Patent Number: 4,568,688
Date of Patent: Feb. 4, 1986

[54] ANTIHYPOTENSIVE TETRAHYDRO-1H-PYRAZOLO[5,1-A]ISOINDOLES

[75] Inventors: Erich Cohnen, Jork; Ben Armah, Hamburg, both of Fed. Rep. of Germany

[73] Assignee: Beiersdorf Aktiengesellschaft, Hamburg, Fed. Rep. of Germany

[21] Appl. No.: 601,188

[22] Filed: Apr. 17, 1984

[30] Foreign Application Priority Data

Apr. 23, 1983 [DE] Fed. Rep. of Germany ....... 3314843

[51] Int. Cl.[4] .................. A61K 31/415; C07D 487/04
[52] U.S. Cl. .................................. 514/402; 514/403; 548/348; 548/369
[58] Field of Search ....................... 548/369, 336, 348; 424/273 P, 273 R; 514/402, 403

[56] References Cited

U.S. PATENT DOCUMENTS 4,075,342  2/1978  Omodei-Salé et al. ......... 548/369 X

OTHER PUBLICATIONS

CAS Registry Handbook for 1965-1971, Published 1974, Chemical Abstracts Service, Columbus, Ohio, p. 3100R.

Primary Examiner—Richard A. Schwartz
Attorney, Agent, or Firm—Sprung Horn Kramer & Woods

[57] ABSTRACT

New substituted tetrahydro-1H-pyrazolo[5,1-a]isoindoles of the formula I

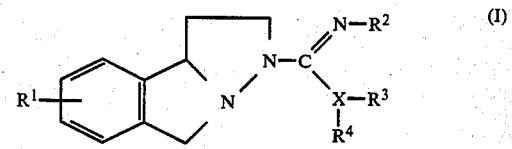

in which $R^1$ denotes a hydrogen or halogen atom or an alkoxy group having 1 to 4 carbon atoms, $R^2$, $R^3$ and $R^4$, which can be identical or different, denote a hydrogen atom or an alkyl group having 1 to 4 carbon atoms, or $R^2$ and $R^3$ together denote the ethylene group, and X denotes a nitrogen atom or a methine group, and their acid addition salts have a long-lasting hypertensive effect and can be used as anti-hypotensives.

12 Claims, No Drawings

ANTIHYPOTENSIVE TETRAHYDRO-1H-PYRAZOLO[5,1,a]ISOINDOLES

The invention relates to new substituted tetrahydro-1H-pyrazolo[5,1-a]isoindoles of the formula I

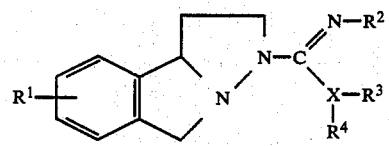

in which $R^1$ denotes a hydrogen or halogen atom or an alkoxy group with 1 to 4 carbon atoms, $R^2$, $R^3$ and $R^4$, which can be identical or different, denote a hydrogen atom or an alkyl group having 1 to 4 carbon atoms, or $R^2$ and $R^3$ together denote the ethylene group, and X denotes a nitrogen atom or a methine group, and their acid addition salts, process for their preparation and their use in pharmaceutical products.

In addition, the invention relates to new compounds of the formula II

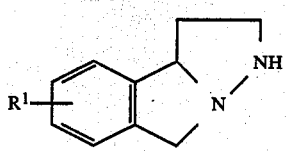

in which $R^1$ has the abovementioned meaning, and their salts, process for their preparation and their use as intermediates for the preparation of the compounds according to the invention and according to claim 1.

Although pharmaceutically tolerated salts of the new compounds of the formula I are preferred, all acid addition salts lie within the scope of the invention. All acid addition salts are valuable for the preparation of the bases, even if the specific salt is only required as an intermediate, such as, for example, when the salt is formed only for purposes of purification or identification, or if it is used as an intermediate for the preparation of a pharmaceutically tolerated salt, such as, for example, by ion exchange procedures.

The new compounds of the general formulae I and II contain asymmetric carbon atoms. Thus the invention also relates to the various optical isomers and the diastereoisomers, as well as to the addition salts of these compounds with acids. Racemates can be resolved into their optical antipodes by methods known per se.

The alkyl groups and the alkyl moieties of the alkoxy groups can be straight-chain or branched according to the invention, and they are preferably methyl or ethyl groups.

The methoxy and ethoxy groups are preferred alkoxy groups.

Halogen is preferably fluorine, chlorine or bromine.

The methyl and ethyl groups are particularly preferred alkyl groups.

$R^1$ is preferably hydrogen. Substituents $R^1$ which do not denote hydrogen are preferably located in the 4-, 6- or 7-position of the phenyl portion of the isoindole radical.

X is preferably nitrogen.

The carboximidamides of the formula I according to the invention, in which X denotes nitrogen, and $R^2$, $R^3$ and $R^4$ denote hydrogen or alkyl, and $R^1$ has the indicated meaning, are particularly preferred.

The imidazolines of the formula I, in which X is nitrogen, and $R^2$ and $R^3$ together denote the ethylene group, and $R^1$ and $R^4$ have the indicated meaning, are also preferred.

In addition, acetamido compounds of the formula I, in which X denotes the methine group, $R^2$, $R^3$ and $R^4$ are hydrogen or alkyl, and $R^1$ has the indicated meaning, are preferred.

The compound 2,3,3a,8-tetrahydro-1H-pyrazolo[5,1-a]isoindole-1-carboximidamide is distinguished by a pronounced therapeutic effect and is particularly preferred.

The new compounds according to the invention and their acid addition salts have valuable therapeutic properties. They are particularly distinguished by a long-lasting hypertensive effect when administered to a warm-blooded organism and can thus be used as antihypotensives for the treatment of hypotension and orthostatic dysregulation.

At a dosage of 0.3–3.0 mg/kg i.v., the new compounds increase the blood pressure of anaesthetised cats by 10–30%; in normotensive rats, 1–10 mg/kg s.c. is followed by a 30% increase in blood pressure which persists for 6 hours.

The compounds can be administered orally or parenterally. The dosage for oral administration to humans is 0.1 to 50 mg, preferably 1 to 10 mg, per day. The substances are advantageously administered in divided doses, for example twice a day.

In addition, the substances according to the invention can, as a consequence of their α-sympathomimetic, vasoconstrictor effect, be used as rhinologicals, in particular in the form of nasal drops. The dosages at the preferred concentration of 1–10 mg/ml, corresponding to a 0.1–1.0% strength aqueous solution, are preferably several drops per nostril several times a day.

According to the invention, pharmaceutical compositions which contain the compound according to claim 1 or its pharmaceutically tolerated salts, together with a pharmaceutically tolerated diluent or vehicle, are produced.

The compounds according to the invention can be mixed with customary pharmaceutically tolerated diluents or vehicles and, where appropriate, with other auxiliaries, and can be administered, for example, orally or parenterally. They can be administered orally in the form of tablets, coated tablets, syrups, suspensions and liquids, or parenterally in the form of solutions or suspensions. Products for oral administration can contain one or more additives, such as sweeteners, flavourings, colorants and preservatives. Tablets can contain the active compound mixed with customary pharmaceutically tolerated auxiliaries, for example inert diluents, such as calcium carbonate, sodium carbonate, lactose and talc, granulating agents and agents which promote the disintegration of the tablets on oral administration, such as starch or alginic acid, binders, such as starch or gelatin, and lubricants, such as magnesium stearate, stearic acid and talc.

Examples of suitable vehicles are lactose, gelatin, maize starch, stearic acid, ethanol, propylene glycol, ethers of tetrahydrofuryl alcohol and water.

The tablets can be coated by known procedures in order to retard the disintegration and absorption in the gastrointestinal tract, and by this means the activity of the active compound can extend over a prolonged period. Likewise, the suspensions of the active compound can be mixed with auxiliaries which are customary for the preparation of compositions of these types, for example suspending agents, such as methylcellulose, tragacanth or sodium alginate, wetting agents, such as lecithin, polyethylene stearate and polyoxyethylene sorbitan monooleate, and preservatives, such as ethyl parahydroxybenzoate. Capsules can contain the active compound as the only constituent or mixed with a solid diluent, such as calcium carbonate, calcium phosphate or kaolin. The injectable products are likewise formulated in a manner known per se. The pharmaceutical products can contain the active compound in an amount of from 0.1 to 90%, in particular 1 to 90%, the remainder being a vehicle or additive. Having regard to the preparation and administration, solid products, such as tablets and capsules, are preferred. The products preferably contain the active compound in an amount of 5 mg.

A process for the preparation of the compounds of the formula I is characterised in that compounds of the formula II

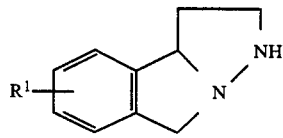

in which $R^1$ has the abovementioned meaning, are reacted with compounds of the general formula (III)

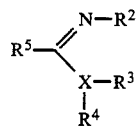

in which $R^2$, $R^3$ and $R^4$ have the abovementioned meaning, and in which $R^5$ denotes a group which can undergo nucleophilic exchange, such as the alkylthio or alkoxy groups.

The methylthio and methoxy groups are preferred groups $R^5$. The reaction is carried out with a hydrohalide of (III) in an alcohol, preferably amyl alcohol, as the solvent, at the boiling point.

The starting compounds of the formula III are known or can be obtained by known processes.

Another process for the preparation of the compounds of the formula I according to the invention, in which $R^2$ denotes hydrogen and X denotes nitrogen, is characterised in that compounds of the formula II having the indicated meaning for $R^1$ are reacted with cyanamide or with substituted cyanamides of the formula NCNR$^3$R$^4$, in which $R^3$ and $R^4$ have the abovementioned meaning. The reaction is preferably carried out in alcohols, with acid addition salts of the compounds of the formula II, at the boiling point. n-Amyl alcohol is particularly preferred.

The substituted cyanamides used as starting compounds are known or can be obtained by known processes.

The process for the preparation of the compounds of the general formula (II) used as intermediates is characterised in that alkyl 2-bromomethylcinnamates of the general formula (IV)

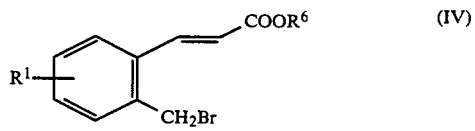

in which $R^1$ has the abovementioned meaning, and $R^6$ denotes a methyl or ethyl group, are reacted with t-butyl carbazate to give substituted isoindolines of the formula (V)

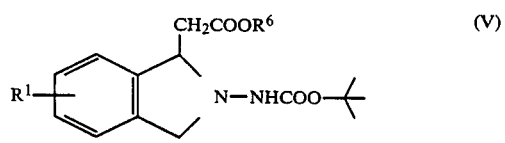

and these are then cyclised with acids to give 2-oxo-2,3,3a-8-tetrahydro-1H-pyrazolo[5,1-a]isoindoles of the formula (VI)

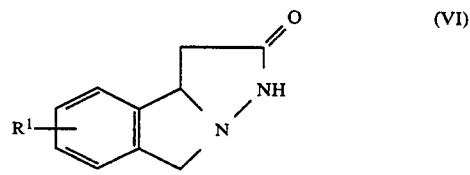

The lactams (VI) are converted into the compounds of the formula (II) by reduction.

The reaction of the unsaturated bromide (IV) with t-butyl carbazate takes place at room temperature in suitable solvents, such as, for example, dimethylformamide, dimethylacetamide and N-methylpyrrolidone. Suitable acids are mineral acids, in particular hydrochloric acid. Particularly suitable reducing agents for the reaction (VI)→(II) are metal hydrides, for example lithium aluminium hydride.

The starting compounds of the formula IV are known or can be obtained by known processes.

The compounds of the general formulae I and II can be isolated from the reaction mixtures either as bases or in the form of their salts. As bases, they can be converted by known processes into the salts using suitable inorganic or organic acids.

A resulting basic compound can be converted into a corresponding acid addition salt, for example by reacting it with an inorganic or organic acid, such as a therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulphuric, phosphoric, nitric or perchloric acid, or organic acids, e.g. carboxylic or sulphonic acids, such as formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, aminosalicylic, embonic, nicotinic, methanesulphonic, ethanesulphonic, hydroxy-ethanesulphonic, ethylenesulphonic, benzenesulphonic, halogenobenzenesulphonic, toluenesulphonic, naphthalenesulphonic and sulphanilic acid; methionine, tryptophan, lysine and arginine.

Salts of the abovementioned acids or other salts, for example the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Physiologically tolerated salts of the compound of the formula I are preferred. Examples of suitable inorganic acids for this are hydrogen halide acids, for example hydrochloric acid, or sulphuric acid, and examples of suitable organic acids are fumaric acid, maleic acid, citric acid and tartaric acid. For their preparation, the alcoholic solution of a suitable acid is added to the hot alkaline solution of the base, and the salt is obtained after addition of ether.

Diastereomers can be separated into their racemic modifications in a known manner on the basis of the physicochemical differences of the constituents, for example by chromatography and/or fractional crystallisation.

Racemates can be resolved according to known methods, for example by recrystallisation from an optically active solvent, with the aid of micro-organisms or by reaction with an optionally active acid which forms salts with the racemic compound, and separation of the diastereoisomers by fractional crystallisation, from which the enantiomers can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Advantageously, the more active of the two antipodes is isolated. According to the invention it is however also possible to obtain the pure enantiomers by asymmetric synthesis.

The examples which follow serve to illustrate the invention:

EXAMPLE 1

2,3,3a,8-Tetrahydro-1H-pyrazolo[5,1-a]isoindole-1-carboximidamide 3.92 g (0.02 mol) of 2,3,3a,8-tetrahydro-1H-pyrazolo[5,1-a]isoindole hydrochloride and 0.95 g of cyanamide in 20 ml of n-amyl alcohol are heated to boiling for 2 hours. After distilling out the solvent, the residue is taken up in boiling ethanol, active charcoal is added, and, after filtration, the filtrate is evaporated in vacuo. After recrystallisation from isopropanol/ethyl acetate, 2.4 g of the hydrochloride of 2,3,3a,8-tetrahydro-1H-pyrazolo[5,1-a]isoindole-1-carboximidamide are obtained. Melting point 233°–234° C.

The following compounds of the formula I were prepared in analogy to Example 1:

| Example | $R^1$ | $R^2$ | $R^3$ | $R^4$ | X | m.p. °C. | Salt |
|---|---|---|---|---|---|---|---|
| 2 | H | H | $CH_3$ | $CH_3$ | N | 181–83 | fumarate |
| 3 | 4-Cl | H | H | H | N | 238–40 | HCl |
| 4 | 7-Cl | H | H | H | N | 270–72 | HCl |
| 5 | 6-$OCH_3$ | H | H | H | N | 280–82 | HCl |

EXAMPLE 6

1-(2-Imidazolin-2-yl)-2,3,3a,8-tetrahydro-1H-pyrazolo[5,1-a]isoindole 4.2 g (0.026 mol) of 2,3,3a,8-tetrahydro-1H-pyrazolo[5,1-a]isoindole and 6.3 g (0.026 mol) of 2-methylthioimidazoline hydroiodide in 50 ml of n-amyl alcohol are heated to boiling for 1.5 hours. After evaporating off the solvent, the residue is taken up in methanol, the solution is treated with active charcoal and the product is finally crystallised from acetone. 2.8 g of the hydroiodide of 1-(2-imidazolin-2-yl)-2,3,3a,8-tetrahydro-1H-pyrazolo[5,1-a]isoindole are obtained. After recrystallisation once more from isopropanol, the melting point is 238°–240° C. (decomposition).

The following carboximidamides of the formula I were prepared in analogy to Example 6 using the S-methylisothiuronium salts of the formula III:

N-Methyl-(2,3,3a,8-tetrahydro-1H-pyrazolo[5,1-a]isoindole-1)-carboximidamide ($R^2$=methyl)

$N^1,N^2$-Dimethyl-(2,3,3a,8-tetrahydro-1H-pyrazolo[5,1-a]isoindole-1)-carboximidamide ($R^2$, $R^3$=methyl).

EXAMPLE 7

1-Acetimido-2,3,3a,8-tetrahydro-1H-pyrazolo[5,1-a]isoindole hydrochloride 3.1 g (0.019 mol) of 2,3,3a,8-tetrahydro-1H-pyrazolo[5,1-a]isoindole and 3.3 g (0.03 mol) of ethyl acetimidate hydrochloride in 100 ml of absolute ethanol are stirred at room temperature for 15 hours. After removing the ethanol, the residue of 1-acetimido-2,3,3a,8-tetrahydro-1H-pyrazolo[5,1-a]isoindole hydrochloride is crystallised using ethyl acetate/isopropanol. Melting point 255°–257° C. (decomposition).

Example 8

2,3,3a,8-Tetrahydro-1H-pyrazolo[5,1-a]isoindole hydrochloride 7.0 g (0.04 mol) of 2-oxo-2,3,3a,8-tetrahydro-1H-pyrazolo[5,1-a]isoindole and 3.8 g of lithium aluminium hydride in 150 ml of absolute tetrahydrofuran are heated to boiling for 4 hours. After cooling, the excess hydride is destroyed with 30% strength NaOH. The precipitate is filtered off, the tetrahydrofuran is evaporated, and the residue is taken up in ethanolic hydrochloric acid. After recrystallisation from isopropanol, 4.0 g of 2,3,3a,8-tetrahydro-1H-pyrazolo[5,1-a]isoindole hydrochloride are obtained. Melting point 166°–167° C. (decomposition).

The following compounds of the formula II were prepared in analogy to Example 8:

4-Chloro-2,3,3a,8-tetrahydro-1H-pyrazolo[5,1-a]isoindole hydrochloride, 7-chloro-2,3,3a,8-tetrahydro-1H-pyrazolo[5,1-a]isoindole hydrochloride, and 6-methoxy-2,3,3a,8-tetrahydro-1H-pyrazolo[5,1-a]isoindole hydrochloride.

EXAMPLE 9

2-Oxo-2,3,3a,8-tetrahydro-1H-pyrazolo[5,1-a]isoindole hydrochloride 20.0 g (0.062 mol) of ethyl N-(t-butyloxycarbonylamino)-2,3-dihydro-1H-isoindole-1-acetate in 50 ml of chloroform are treated with 200 ml of concentrated hydrochloric acid for 15 hours, with vigorous stirring. The solvent is removed in vacuo, and the product is recrystallised from isopropanol/ethyl acetate. Yield: 9 g of 2-oxo-2,3,3a,8-tetrahydro-1H-pyrazolo[5,1-a]isoindole hydrochloride. Melting point 216°–218° C. (decomposition).

The following compounds of the formula VI were prepared in analogy to Example 9:
2-oxo-4-chloro-2,3,3a,8-tetrahydro-1H-pyrazolo[5,1-a]isoindole hydrochloride, melting point 242°–244° C. (decomposition),
2-oxo-7-chloro-2,3,3a,8-tetrahydro-1H-pyrazolo[5,1-a]isoindole hydrochloride, melting point 222°–224° C. (decomposition), and
2-oxo-6-methoxy-2,3,3a,8-tetrahydro-1H-pyrazolo[5,1-a]isoindole hydrochloride, melting point 218°–220° C. (decomposition).

EXAMPLE 10

Ethyl N-(t-butyloxycarbonylamino)-2,3-dihydro-1H-isoindole-1-acetate 21.8 g (0.08 mol) of ethyl 2-bromomethylcinnamate and 26.4 g (0.20 mol) of t-butyl carbazate in 300 ml of dimethylformamide are stirred at room temperature for several days until the reaction is complete. The dimethylformamide is evaporated off in vacuo, the residue is partitioned between water and chloroform, and the residue of the organic phase is purified by preparative HPLC on silica gel. Yield: 22.0 g of ethyl N-(t-butyloxy-carbonylamino)-2,3-dihydro-1H-isoindole-1-acetate (oil).

The following compounds of the formula V were prepared in analogy to Example 10:
Ethyl N-(t-butoxycarbonylamino)-4-chloro-2,3-dihydro-1H-isoindole-1-acetate,
ethyl N-(t-butoxycarbonylamino)-7-chloro-2,3-dihydro-1H-isoindole-1-acetate and
ethyl N-(t-butoxycarbonylamino)-6-methoxy-2,3-dihydro-1H-isiondole-1-acetate.

EXAMPLE 11

Preparation of tablets

Tablets which contain the constituents mentioned below can be prepared in a known manner. They can be used for the treatment of hypotensive conditions at a dose of 1 to 2 tablets once a day.

2,3,3a,8-Tetrahydro-1H-pyrazolo[5,1-a]isoindole-1-carboximidamide: 5 mg;
Lactose: 75 mg;
Maize starch: 10 mg;
Microcrystalline cellulose: 8 mg;
Polyvinylpyrrolidone: 1 mg;
Magnesium stearate: 0.5 mg;
Highly disperse silica: 0.5 mg;

EXAMPLE 12

Preparation of ampoules

Ampoules which contain the constituents mentioned below can be prepared in a known manner. The active compound and sodium chloride are dissolved in water and dispensed into glass ampoules under nitrogen. They can be used for the treatment of hypotensive conditions at a dose of 1 to 2 ampoules twice a day.

2,3,3a,8-Tetrahydro-1H-pyrazolo[5,1-a]isoindole-1-carboximidamide: 2.5 mg
Sodium chloride: 18 mg
Distilled water ad: 2.0 ml

EXAMPLE 13

Nasal drops which contain the constituents mentioned below can be prepared in a known manner. They can be used at a dose of two to three drops per nostril twice to four times a day.

2,3,3a,8 -Tetrahydro-1H-pyrazolo[5,1-a]isoindole-1-carboximidamide: 0.25 g
Methylcellulose: 1.0 g
Distilled water ad: 100 ml

We claim:

1. A substituted tetrahydro-1H-pyrazolo[5,1-a]isoindole of the formula I

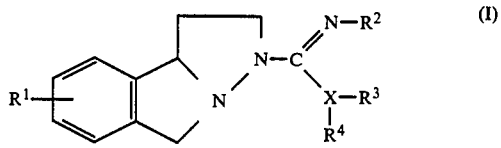

in which $R^1$ denotes a hydrogen or halogen atom or an alkoxy group having 1 to 4 carbon atoms, $R^1$, $R^3$ and $R^4$, which can be identical or different, denote a hydrogen atom or an alkyl group having 1 to 4 carbon atoms, or $R^2$ and $R^3$ together denote the ethylene group, and X denotes a nitrogen atom or a methine group, or an acid addition salt thereof.

2. A compound of the formula II

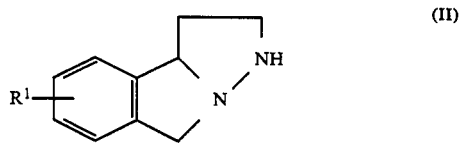

in which $R^1$ denotes a halogen atom or an alkoxy group having 1 to 4 carbon atoms, or an acid addition salt thereof.

3. A compound of claim 1 which is 2,3,3a,8-tetrahydro-1H-pyrazolo[5,1-a]isoindole-1-carboximidamide.

4. A compound of claim 1 which is 2,3,3a,8-tetrahydro-1H-pyrazolo[5,1-a](4-chloroisoindole)-1-carboximidamide.

5. A compound of claim 1 which is 2,3,3a,8-tetrahydro-1H-pyrazolo[5,1-a](7-chloroisoindole)-1-carboximidamide.

6. A compound of claim 1 which is 2,3,3a,8-tetrahydro-1H-pyrazolo[5,1-a](6-methoxyisoindole)-1-carboximidamide.

7. A pharmaceutical composition comprising a hypertensively effective amount of a compound of claim 1 or a physiologically tolerated acid addition salt thereof together with an inert pharmaceutical vehicle.

8. A pharmaceutical composition of claim 7 in oral unit dosage form.

9. A pharmaceutical composition comprising an amount of a compound of claim 1 or a physiologically tolerated acid addition salt thereof, effective for providing an α-sympathomimetic vasoconstrictor effect, together with an inert pharmaceutical vehicle.

10. A pharmaceutical composition of claim 9 in the form of nasal drops or sprays.

11. A method for the treatment of hypotension in a warm-blooded organism requiring said treatment, which comprises administering to said warm-blooded organism a hypertensively effective amount of a compound of claim 1 or a physiologically tolerated acid addition salt thereof.

12. A method for providing an α-sympathomimetic vasoconstrictor effect in a warm-blooded organism requiring said treatment which comprises administering to said warm-blooded organism an amount of a compound of claim 1 or a physiologically tolerated acid addition salt thereof, effective for providing an α-sympathomimetic vasoconstrictor effect.

* * * * *

UNITED STATES PATENT AND TRADEMARK OFFICE
CERTIFICATE OF CORRECTION

PATENT NO. : 4,568,688

DATED : February 4, 1986

INVENTOR(S) : Erich Cohnen, et al.

It is certified that error appears in the above-identified patent and that said Letters Patent is hereby corrected as shown below:

Title page, under "U.S. Patent Documents"  Delete "Omodei-Sale et al." and substitute -- Sale et al. --

Col. 8, line 23   Delete "$R^1$" and substitute --$R^2$--

Signed and Sealed this

Twenty-ninth Day of July 1986

[SEAL]

Attest:

*Attesting Officer*

DONALD J. QUIGG

*Commissioner of Patents and Trademarks*